(12) United States Patent
Gao et al.

(10) Patent No.: US 7,131,467 B2
(45) Date of Patent: Nov. 7, 2006

(54) INSTRUMENT FOR APPLYING A TIE TO TWO ITEMS AND METHOD OF MAKING SAME

(75) Inventors: Hua Gao, Milwaukee, WI (US); James A. Rinner, Racine, WI (US)

(73) Assignee: Pilling Weck Incorporated, Horsham, PA (US)

( * ) Notice: Subject to any disclaimer, the term of this patent is extended or adjusted under 35 U.S.C. 154(b) by 410 days.

(21) Appl. No.: 10/490,583

(22) PCT Filed: Oct. 24, 2002

(86) PCT No.: PCT/US02/34094

§ 371 (c)(1),
(2), (4) Date: Mar. 22, 2004

(87) PCT Pub. No.: WO2004/037463

PCT Pub. Date: May 6, 2004

(65) Prior Publication Data

US 2004/0267286 A1 Dec. 30, 2004

(51) Int. Cl.
*B21F 15/04* (2006.01)
(52) U.S. Cl. .................................. 140/118; 140/123.5
(58) Field of Classification Search ................ 140/117, 140/118, 119, 120, 123, 123.5
See application file for complete search history.

(56) References Cited

U.S. PATENT DOCUMENTS

| 1,120,575 A | 12/1914 | Wertz |
| 1,304,620 A | 5/1919 | Steingenic |
| 1,365,649 A | 1/1921 | Bates |
| 1,463,869 A | 8/1923 | Campbell |
| 2,049,361 A | 7/1936 | Ericsson |
| 2,279,068 A | 7/1942 | Siebrandt |
| 2,291,413 A | 7/1942 | Siebrandt |
| 2,455,609 A | 12/1948 | Scheib |
| 2,657,718 A | 11/1953 | Greathouse |
| 2,892,284 A | 6/1959 | Shawhan |
| 3,273,605 A | 9/1966 | Feraara |
| 3,507,270 A | 4/1970 | Ferrier |
| 3,759,302 A | 9/1973 | Attenborough |
| 3,865,155 A | 2/1975 | Saath |
| 4,527,554 A | 7/1985 | Klein |
| 4,880,038 A | 11/1989 | Meinershagen |
| 4,935,027 A | 6/1990 | Yoon |
| 5,004,020 A | 4/1991 | Meinershagen |

(Continued)

OTHER PUBLICATIONS

U.S. Appl. No. 10/158,470, Instrument and Method for Pulling and Twisting Tie Onto Two Separated Items-Four Drawing Sheets, Figs. 1-4 Showing The Instrument.

*Primary Examiner*—Lowell A. Larson
(74) *Attorney, Agent, or Firm*—Baker & Hostetler LLP

(57) ABSTRACT

An instrument for applying a tie (12) to two items (10, 110), and a method of making same. The instrument is arranged for pulling separated bones or other items together and securing them together by twisting a tie onto them. The instrument can be made of plastic and it need not include any threaded parts. It can have two handles (21, 22) with a tie gripper (24) and a tie guide (26) on respective ones of the handles which can be squeezed together for pulling on a tie to draw separated items together. The handles rotate together, and there can be a crank (27) for effecting the rotation and thereby twist the tie onto the items.

25 Claims, 6 Drawing Sheets

U.S. PATENT DOCUMENTS

| | | |
|---|---|---|
| 5,275,383 A | 1/1994 | Wick et al. |
| 5,449,361 A | 9/1995 | Preissman |
| 5,501,688 A | 3/1996 | Whiteside |
| 5,741,279 A | 4/1998 | Gordon |
| 5,849,012 A | 12/1998 | Abboudi |
| 5,935,133 A | 8/1999 | Wagner |
| 6,383,208 B1 | 5/2002 | Sancoff |

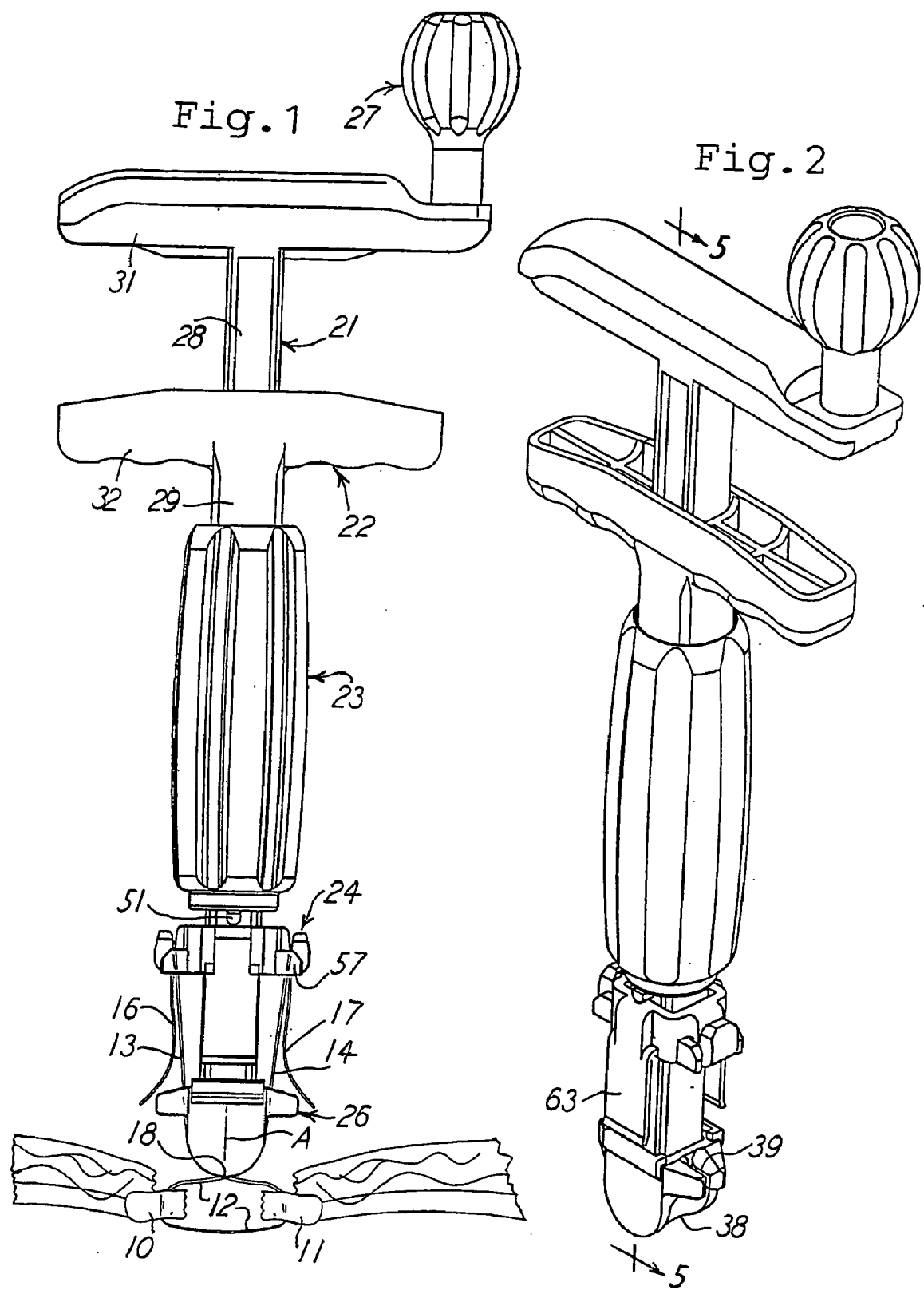

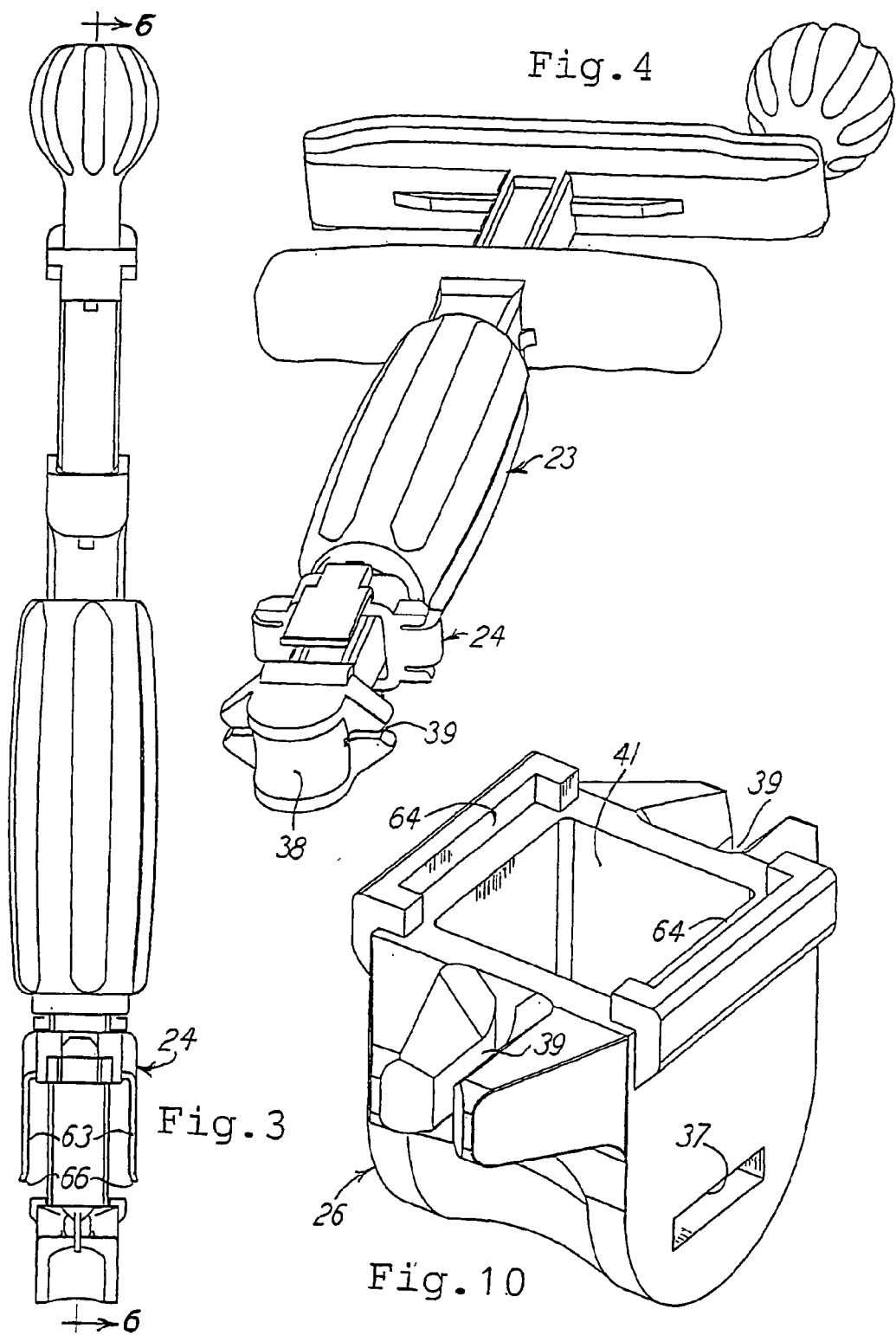

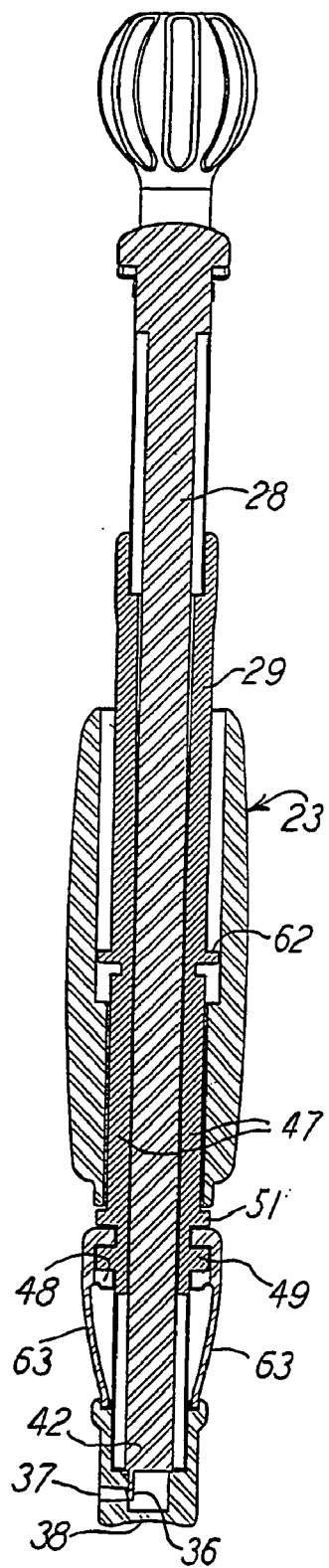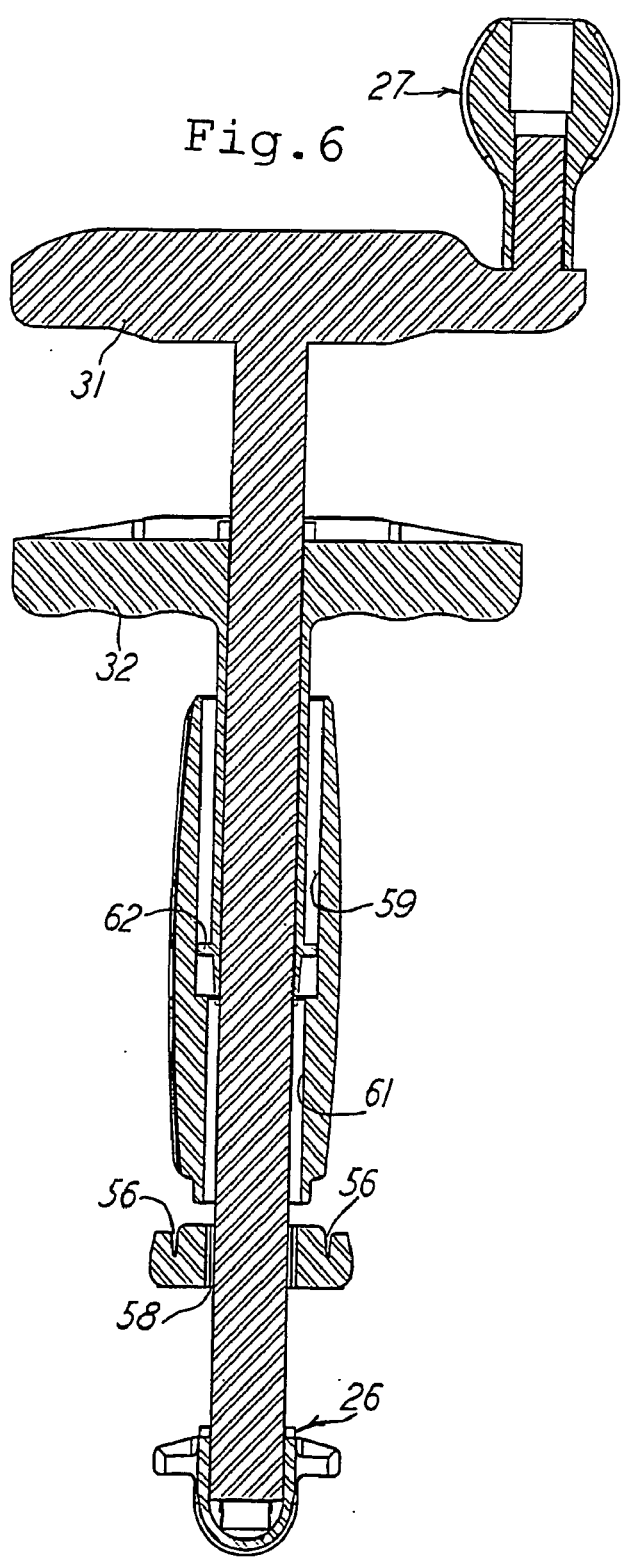

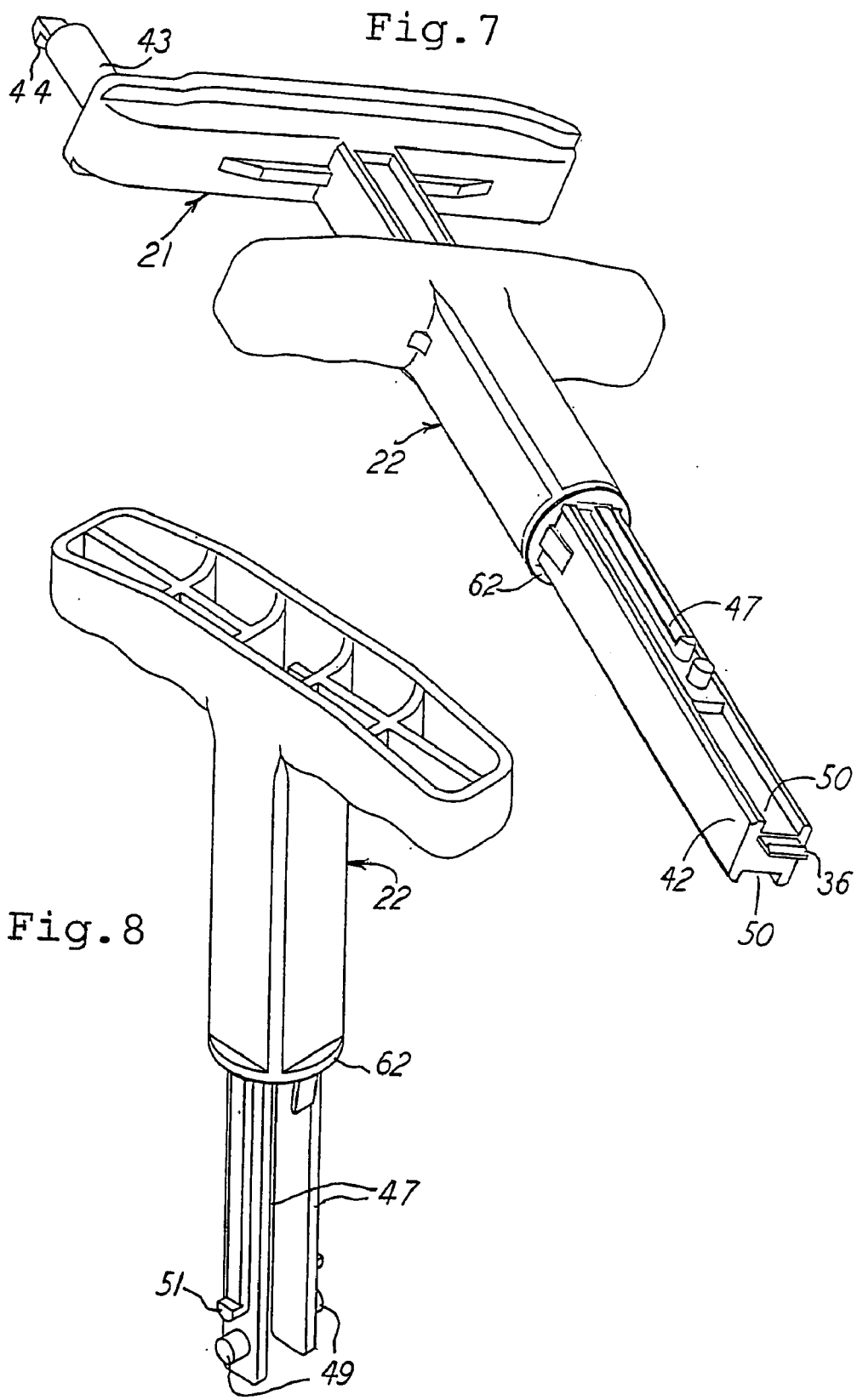

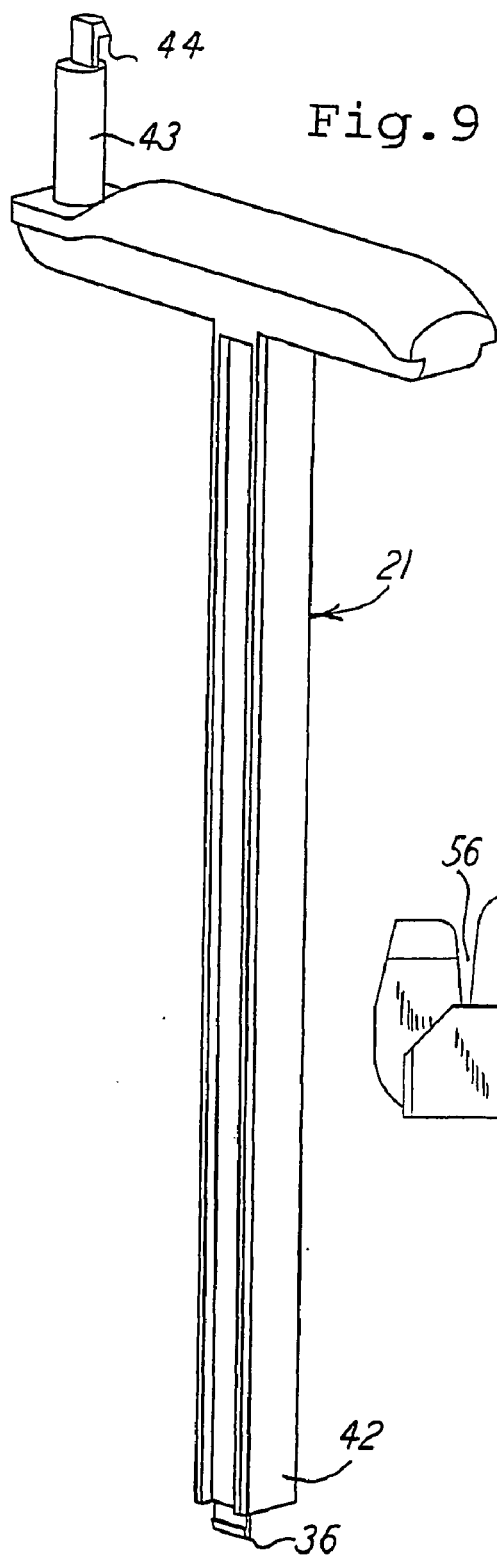
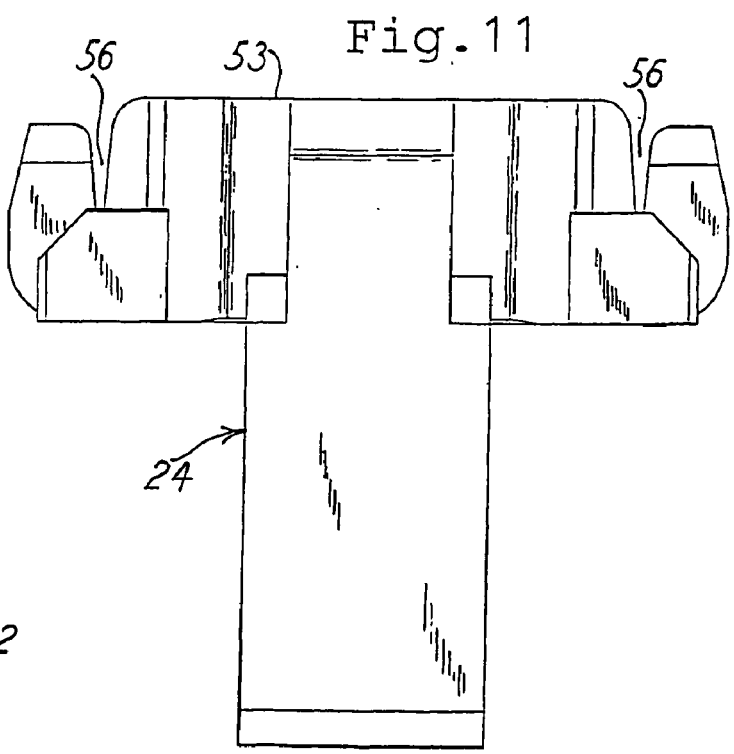

INSTRUMENT FOR APPLYING A TIE TO TWO ITEMS AND METHOD OF MAKING SAME

This invention relates to an instrument for applying a tie to two items and method of making same. More particularly, it relates to an instrument and the method wherein a tie is pulled for drawing the two items together, and the tie is then fixedly twisted onto itself for securing it to the items. This instrument is thus utilized in helically twisting a tie, wire, suture, or the like onto itself after the tie is secured to the item to be tied.

For further reference, our U.S. patent application Ser. No. 10/158,470, filed May 31, 2002, and now U.S. Pat. No. 6,752,810, issued Jun. 22, 2004 can be considered.

BACKGROUND OF THE INVENTION

There are many conditions where a tie, such as a wire, suture, cable, or like strand capable of being secured onto itself by twisting, is required to hold items together. One such condition is in the medical field where a patient's sternum has been separated for heart surgery and it is then necessary to pull the separated parts of the sternum together and to then twist sutures onto the sternum to hold the sternum together for natural healing by knitting. The present invention is particularly useful in the medical field under conditions where any bone is separated, and it will be basically described in that context. Of course, it will also be disclosed for and cover applications in any field where a tie is to twisted onto itself for securement.

Thus, the present invention provides and instrument, and method of making same, wherein a tie or suture can be readily and accurately installed on items or bone and then tensioned to draw the items or broken bones together and to ultimately twist the tie or suture onto itself in a helical pattern to tie the items or bones together. The twisting is accomplished by progressively twisting along the tie in even knots and without the incidence of breaking the tie during twisting.

With this invention, the items or bones are drawn together and the tie or suture is then twisted onto itself. Thus, there is no slack or Looseness in the tie or suture relative to the items or bone, and there is an even and balanced pull on the tie, and that is all accomplished in an efficient and rapid manner with optimum accuracy though only a minimum of user skill.

The tie is strung and connected to the exterior of the instrument, and it is not strung through the interior of an instrument. Thus, the stringing and attaching of the wire are easily and accurately accomplished relative to the instrument. Also, the wire tie or suture is strung in a position to effect optimum pulling force on the items or bone for drawing the items together under easily applied tension in the tie.

In this invention, the tensioning of the tie is accomplished by a squeezing action through the hand of the user, and, with that same squeezing grip on the instrument, the user can also twist the tie onto itself in a helical pattern. With only one gripping action by the user, the tie tensioning and initial twisting are accomplished. So there is the initial tensioning in the tie to draw the items or bone together, and there is then the twisting of the tie while maintaining that tension, and then a rotation action is applied to form the helical twisting of the tie to secure the tie on the items or bone.

Of further importance in this invention, is the method of making the instrument. In this regard, the various parts of the instrument are easily and reliably manufactured and they are also easily and reliably assembled. These and like desirable accomplishments are important because they permit the instrument to be made with a minimum of expense for material and instrument parts and minimum skill both in manufacturing and in assembling the instrument. In fact, this instrument can be considered to be a disposable instrument with a one-time usage, and that is particularly important in the medical field where sterility and expense are usually significant where a long lifetime instrument is made. While the instrument is sufficiently sturdy to apply the required pull and twist actions, the instrument can be made of plastic material.

BRIEF DESCRIPTION OF THE DRAWINGS

FIG. 1 is a front elevation view of the instrument of this invention, showing it with a tie and being applied to a separated sternum, the remaining views are without the tie and sternum.

FIG. 2 is a right side perspective view of FIG. 1.

FIG. 3 is a right side elevation view of FIG. 1.

FIG. 4 is a bottom perspective view of FIG. 1.

FIG. 5 is a section view taken on a plane designated by the line 5—5 of FIG. 2, but with two parts at the lower end in positions different from those of FIG. 2.

FIG. 6 is a section view taken on a plane designated by the line 6—6 of FIG. 3.

FIG. 7 is a bottom perspective view of two FIG. 4 parts.

FIG. 8 is a top perspective view on one part of FIG. 7.

FIG. 9 is a top perspective view of one part of FIG. 7.

FIG. 10 is an enlarged front perspective view of a part seen at the bottom of FIG. 2, but from the back side.

FIG. 11 is an enlarged front view of a part at the lower end of FIG. 1.

DESCRIPTION OF AN EMBODIMENT AND THE METHOD

Figure 13:
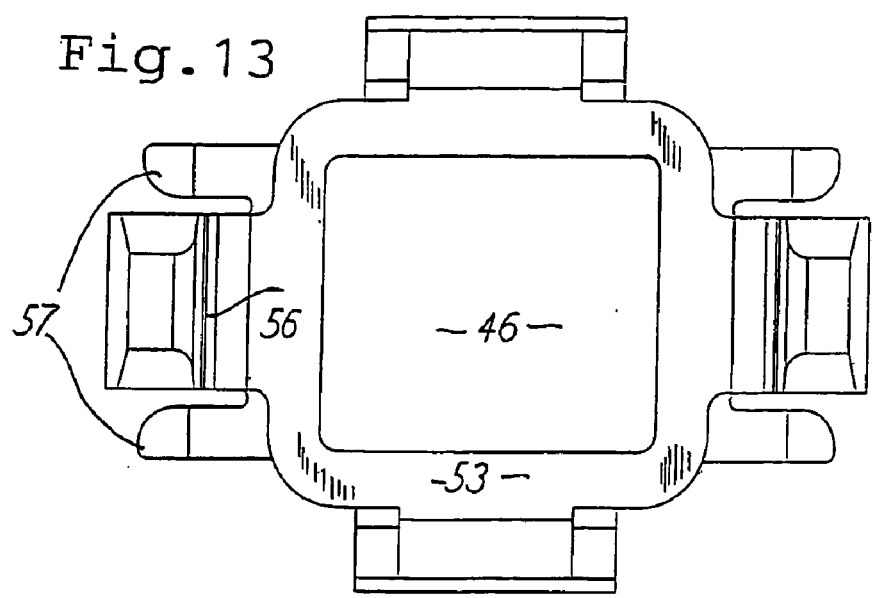
FIG. 13 is a top plan view of FIG. 12.
Figure 12:
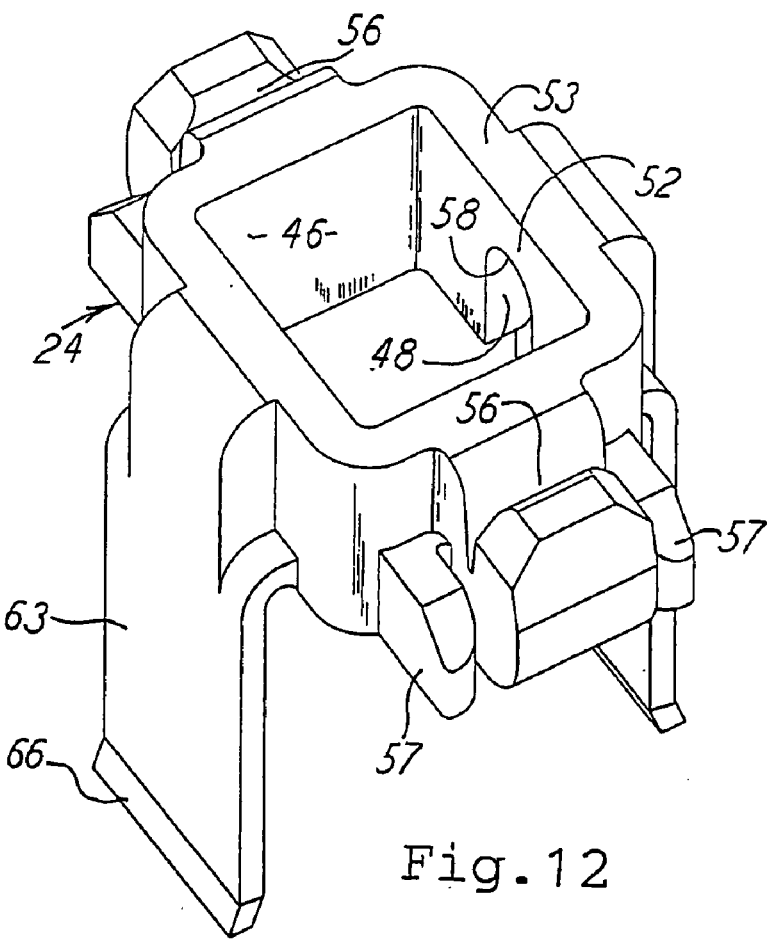
FIG. 12 is an enlarged perspective view of a part at the lower end of FIG. 2.

As mentioned, this invention is useful in the medical field, and it is described in that context. However, it will be readily understood that the invention applies to any field for pulling and twisting a tie or strand for securing two items together. A generic use of the words tie, strand, suture, wire or the like is employed because any such line-type material capable of being tensioned for pulling on two separated items to pull them together, and to then hold them together, and twisting the strand in a helical pattern onto itself, applies in this invention. The strand is capable of being flexed and retain its flexed position, such as being helically twisted onto itself for binding. Thus, this instrument will be found to be useful in various applications of twisted strands and they are included in this coverage.

FIG. 1 shows the instrument being applied to two separated portions 10 and 11 of a sternum with shown ribs and the patient's skin. A tie 12 is strung through the sternum and is crossed upon itself at the longitudinal axis A and extends in two upright portions 13 and 14, and the strand has two terminal ends 16 and 17. The shown instrument is in contact with the tie 12 at least adjacent the crossover location 18. The surgeon would string the tie 12 as disclosed, and that cold be by forceps guiding the tie through the sternum and crossing the tie onto itself and attaching the tie ends to the instrument, all as shown. It will be seen the tie adjacent the sternum extends in substantially horizontal extents which are substantially transverse to the axis A and can be less than five degrees off the horizontal. Thus, when tension is placed in the tie 12, the force on the sternum will be at the optimum angle to pull the sternum parts 10 and 11 toward each other, that is, to pull the sternum together for its subsequent healing. That is all achievable because the instrument has a narrow lower end which can be accurately directed and positioned close to the sternum.

It should be understood that this instrument can be employed for pulling together separated parts of many other materials, other than for use only in the medical field. It could be used in any project where a tie is to be applied to pull parts together and to subsequently twist the tie onto itself and relative to the parts. The material of the tie can be stainless steel, such as in the medical use, and it can also be any material capable of withstanding adequate tension for the project, and it is capable of flexing and twisting onto itself and retaining the twisted position in multiple helical twists extending progressively away from the closed parts, such as in the art of manual twisting of wire onto a sternum. In this description relative to a sternum, or other bone, the tie is considered to be a suture, and in all instances the tie is a strand of suitable material for the closer project.

After the tie is pulled to have adequate tension in it to thereby pull the sternum parts together, as hereinafter described, then the following should be noted. At this time it will also be mentioned that the tie 12 is crossed over relative to itself at 18 in a pattern of where the extent 13 is forward relative to the extent 14 which is therefore further back, as viewed in FIG. 1. So looking down along the axis A and viewing it to have extent 13 on the left in that downward view, the initiation of a clockwise crossover at 18 will be seen. So rotation about the axis A in that clockwise direction, say for a half turn, that is, 180 degrees, will produce the helical twisting of the tie 12 onto itself in a full turn to secure the parts together. That rotation is described hereinafter and is accomplished with the instrument, but only after the instrument is employed to place tension in the tie 12 and pull the separated parts together, instead of having the parts separated, as shown.

Thus there is an initial crossover of the tie in a predetermined pattern so that the subsequent one-half rotation will induce a twist of one full turn, and that will be secure, though additional helical twists can be added thereto.

The instrument can be made of suitable plastic material, such as by molding, and it is shown to consist of only six parts, namely, a first handle 21, a second handle 22, a stable handle 23, a tie gripper 24, a tie engaging head 26, and a cranking knob 27. It can be made and assembled without any threaded fasteners or the like, and the parts can be latched or snapped together, as shown. The handle cross portions 31 and 32 are disposed to be within the span or reach of the user's one hand which thus simultaneously spans the two portions 31 and 32. So one hand guides the instrument while the other hand can be used to string the tie onto the instrument, as shown in FIG. 1 in the shown tie extents.

The handles 21 and 22 are T-shaped with respective stems 28 and 29 telescoped and slidable relative to each other along axis A, and the handles have respective cross portions 31 and 32. The handle stems 28 and 29 are suitably nested together and they can be rectilinear in cross section so they remain in their rotated positions relative to each other and about axis A, and they do not rotate about each other, though they do rotate together in unison about axis A. Of course, the crank knob 27 is used to apply rotation to the handle 21 and thus also to the handle 22.

The lower end of the handle 21 is slightly flexible and it has a barb or detent 36, as seen in FIGS. 5, 7, and 9, and the handle 21 snaps into engagement with the tie head 26 by having the detent 36 received in a notch or opening 37 in the head 26. In that manner, the head 26 is assembled with and actually can be readily released from the handle 21. The head 26 has a compound curved surface 38 at its lower end, and it is that surface 38 that can engage and guide the tie 12 which therefore nests with the guide 26. The guide 26 also has two slots 39 spaced from the axis A and on opposite sides thereof for receiving the tie 12 which is strung into the slots 39. Thus the guide 26 is attached to the handle 21, and they have the respective rectilinear cross sections consisting of the female opening 41 on the guide 26 and male extension 42 on the handle 21, shown for stabilizing the guide 26 on the handle 21 through a snug relationship.

Throughout this disclosure it will be seen and understood that no threaded parts are required. It will also be noticed that the knob 27 attaches to a post 43 on the handle 21 through a barb 44 on the post 43 for the knob 27 to be rotatable on the post 21 for the cranking action of turning the two handles 21 and 22 and the guide 26, all as one unit.

So the parts disclosed herein are sufficiently flexible to achieve the snap or hooking connections being described.

The tie gripper 24 is attached in the assembly by having a rectilinear opening 46 through which two flexible legs 47 of the handle 22 pass for rotational drive connection between the handles 21 and 22 and the gripper 24. The respective leg 47 is slidable in a longitudinal groove 50 on each side of the handle 21, as seen in FIG. 7. To secure the handle 22 and the gripper 24 against movement relative to the handle 22 along the axis A, the gripper 24 has two downwardly facing slots 48 and the handle 22 has two pins 49 which are positioned into the respective slot 48. Also, the handle 22 has two projections 51 above the pins 49 and spaced from the pins 49 the amount of the wall height 52, between the slots 48 and the top surface 53 of the gripper 24. Thus the gripper is trapped between the pins 49 and the projections 51, so it is axially set relative to the handle 22. This can be a snap fit, and the pins 49 and projections 51 are on the two relatively flexible legs 47 on the handle 22.

The gripper 26 has two tie gripping portions which include two V-shaped slots 56,for receiving the tie 12. Also, two side guide bars 57 flank each slot 56 to constrict the tie 12 relative to the slots 56 and thereby assure secure gripping of the tie 12. As seen in FIGS. 5 and 6, the gripper 24 is against the handle legs 47, so it can not move or rock in that plane, but it is slightly clear in the other direction at 58, as seen in FIG. 6, so it can rock in that plane. That rocking direction is compatible with the location of the V-slots which hold the tie 12, so, upon pulling on the tie 12, as hereinafter explained, the gripper will rock to self-adjust to the tension in it and thereby apply an even pulling force relative to the two tie ends 13 and 14. That assures that the following twisting will be on center and even and progress along the axis A.

That rocking is possible because the pins 49 and the projections 51 all present a circular surface adjacent the gripper respective surfaces 53 and 58 which is at the top of the slot 48. So the gripper is self-adjusting in response to the tension in the tie 12.

FIG. 5 and 6 also show that the stabilizing handle 23 is piloted on the handles 21 and 22. The handle 23 is cylindrical and has two axially aligned hollow interiors 59 and 61, and it telescopes over the lower ends of the handles 21 and 22. A circular flange 62 on the handle 22 is snugly received in the handle hollow 59, for guidance, and the widest part of the handle 22 is received in the hollow 61, all for rotatably mounting the handle 23 relative to the handles 21 and 22. The arrangement is such that in the cranking action for the twisting mentioned, the handle 23 is gripped by the user's one hand while the other hand operates the crank knob 27 to rotate the instrument about the axis A. The entire instrument rotates, except for the handle 23, and the tie orbits the axis A.

The handle 23 is free to move slightly along the axis A. and it will rest downwardly on the projections 51, as seen in FIGS. 1 and 5, and it can move upwardly to be stopped by the flange 62.

The gripper 24 has two depending legs 63 which are flexible and flat in one plane thereof as seen in FIGS. 2 and 3. FIG. 10 shows that the guide had two upwardly facing pockets or notches 64, or there can be any entrapment, and each receives the lower and outward turned end 66 of each leg 63. The structure is such that the gripper 24 can be lowered toward the guide 26, by virtue of lowering the handle 22, and the ends 66 can be squeezed toward each other to be received by the notches 64. The gripper is then being held level relative to the entire instrument, and, because at that time the gripper slots 39 are closest to the guide 26, the tie can be snugly applied onto the instrument. So the wide legs 63 act as a restrictor and thereby stabilize the gripper 24 against the rocking action mentioned and lock the device at neutral position for capturing the tie or wire. That construction provides for a releasable attachment between the instrument and the gripper 24, and the release is automatic.

With that connection, the handle 22 and its gripper 24 are frictionally held downward toward the guide 26 and they are then generally lowered relative to the remainder of the instrument. In the lowered mode, the entire instrument can be pressed downward while the tie is being strung, and it can then be snugly strung. Then, when the handles 21 and 22 are squeezed together, the gripper 24 and the guide 26 move away from each other and they put tension into the tie 12, and they pull the tie 12 on the separated parts in the horizontal direction, as mentioned at the outset. Then one-half turn of the entire instrument is made about the axis A to move the tie about the cross-over location and thereby secure the tie in what is then one full urn. It will be noticed that there is therefor a releasable attachment for the gripper 24, and the release is automatic.

The sequence of events can be: the instrument is aimed at the separated parts with the gripper 24 positioned in its lowered positioned; the tie 12 is strung onto the instrument relative to the guide 26 and the tie crosses itself in a selected cross-over direction and the tie is strung through the gripper slots 56; lifting up on the instrument through handle 21 adjusts tension in the tie; squeezing handles 21 and 22 together pulls on the tie to pull the separated work piece parts together; rotating the instrument one-half turn in a continuation of the cross-over direction creates the first twist and securely binds; holding at stabilizing handle 23 and lifting up on it and rotating crank knob 27 causes the tie to twist further onto itself and along axis A; release the tie from the instrument and trim the tie as desired.

The method of making the instrument is inherent in the foregoing, and, in additional explanation, one should notice that the instrument and the method are such that the instrument need not be made of plastic material and it can include threaded parts, if desired. Where so-called snap or latched connections are described, there may be other arrangements for connecting any two parts together within the context of the relative relationship of the various parts.

The method assembly steps can include providing the first handle 21 with its barb 36, or suitable connector, and its knob 27 will eventually be attached; stabilizing handle 23 can be telescoped onto handle 22 from underneath by inwardly flexing handle legs 47 and moving handle 23 to where it is above the projections 51, as shown in the assembly views; gripper 24 can be slid onto the lower end of the handle 22, again having the legs 47 flex inwardly for necessary clearance, and the projections 51 will be above the gripper surface 53 and the pins 49 will be in the gripper slots 48; handle 21 can be slid into handle 22 with the, grooves 50 receiving the legs 47 of the handle 22; and guide 26 can be slid onto the lower end of handle 21 to engage the barb 36 in the guide slot 37.

What is claimed is:

1. An instrument for applying a tie to two items to pull and secure the items together where the items have the tie connected thereto, comprising an assembly of all of the following parts:
    a first handle and a second handle relatively movable along and rotatable about an axis,
    a tie guide attached to said first handle for directing the tie in having the tie cross over upon itself at a location on said axis,
    a tie gripper attached to said second handle for securing the tie to said gripper and thereby to said second handle,
    said tie guide and said location and said gripper all being sequentially spaced from each other along said axis and to be sequentially disposed in a direction away from the separated items,
    a releasable connector operatively connected between said handles for temporarily holding said gripper and said guide in a first spaced relationship along said axis, and
    said connector being operatively releasable for movement between said gripper and said guide to a second spaced relationship along said axis and with the spacing of said second spaced relationship being greater than the spacing of said first spaced relationship to thereby pull on the tie to pull the items together when moving to said second spaced relationship.

2. The instrument for applying a tie, as claimed in claim 1, including:
    a rotator connected to said handles for rotating said handles and said guide and said gripper all in unison and about said axis for twisting the tie onto itself for securing the application of the tie to the items.

3. The instrument for applying a tie, as claimed in claim 2, wherein:
    said rotator is a crank connected to said handles for the rotating.

4. The instrument for applying a tie, as claimed in claim 3, including:
    a third handle rotatably mounted on said first and said second handles for guiding the instrument while rotating.

5. The instrument for applying a tie, as claimed in claim 1, wherein:
    said connector is self-operatively releasable in response to the movement between said gripper and said guide.

6. The instrument for applying a tie, as claimed in claim 1, wherein:
    said handles have respective portions adjacent each other for being-squeezed together to move said handles relatively to each other along said axis and thereby pull on the tie.

7. The instrument for applying a tie, as claimed in claim 1, wherein:
said assembly is free of any threaded attachments and connections.

8. The instrument for applying a tie, as claimed in claim 7, wherein:
said assembly is entirely of plastic material and the attachments and connections includes detents for snapping together and thereby the instrument is made to be disposable after only one use in the medical application thereof.

9. The instrument for applying a tie, as claimed in claim 1, wherein:
said attachments and said connections of said assembly are interlocking latches for hooking together.

10. The instrument for applying a tie, as claimed in claim 1, including:
said gripper being attached to said second handle for rocking motion relative to said second handle to thereby automatically adjust to any tension in the tie attached to said gripper when said gripper is moving to said second spaced relationship, and
a restrictor operative on said gripper for detering the rocking motion when said gripper is in said first spaced relationship.

11. The instrument for applying a tie, as claimed in claim 1, including:
said guide having slots thereon spaced from said axis for stringing reception of the tie to thereby impose orbital motion to the tie upon rotation of said handles.

12. The instrument for applying a tie, as claimed in claim 1, wherein:
said guide is non-movably affixed relative to said first handle and is formed to have the tie nest therewith.

13. An instrument for applying a tie to two items for pulling and securing the items together where the items have the tie connected thereto, comprising an assembly of all of the following parts:
a first handle and a second handle telescoped together by having said first handle extend through and beyond said second handle in a terminal end and with said handles relatively movable along and rotatable about an axis,
a tie guide attached to said terminal end of said first handle for directing the tie in having the tie cross over upon itself at a location on said axis,
a tie gripper attached to said second handle for securing the tie to said gripper and thereby to said second handle,
said guide and said gripper both having tie receptors accessible from the exteriors thereof for stringing the tie thereon free of any need for releasing the tie during the stringing,
said tie guide and said location and said gripper all being sequentially spaced from each other along said axis and to be sequentially disposed in a direction away from the separated items,
said gripper being movable along said axis and relative to said guide and in response to and upon movement of said second handle along said axis for thereby pulling on said tie to pull the items together, and
said assembly being rotatable about said axis as a single unit and initially in a one-half turn in a direction of continuing the cross over so the tie is twisted upon itself and doing so while said gripper is still pulling on said tie.

14. The instrument for applying a tie, as claimed in claim 13, including:
a releasable connector operatively connected between said handles for temporarily holding said gripper and said guide in a first spaced relationship along said axis, and
said connector being operatively releasable for movement between said gripper and said guide to a second spaced relationship along said axis and with the spacing of said second spaced relationship being greater than the spacing of said first spaced relationship to thereby pull on the tie to pull the items together when moving to said second spaced relationship.

15. The instrument for applying a tie, as claimed in claim 14, wherein:
said connector is self-operatively releasable in response to the movement between said gripper and said guide.

16. The instrument for applying a tie, as claimed in claim 13, including:
a rotator connected to said handles for rotating said handles and said guide and said gripper all in unison and about said axis for twisting the tie onto itself for securing the application of the tie to the items.

17. The instrument for applying a tie, as claimed in claim 15, wherein:
said rotator is a crank connected to said handles for the rotating.

18. The instrument for applying a tie, as claimed in claim 17, including:
a third handle rotatably mounted on said first and said second handles for guiding the instrument while rotating.

19. The instrument for applying a tie, as claimed in claim 13, wherein:
said handles have respective portions adjacent each other for being squeezed together to move said handles relatively to each other along said axis and thereby pull on the tie.

20. The instrument for applying a tie, as claimed in claim 13, wherein:
said assembly has snap attachments and connections and is free of any threaded attachments and connections.

21. The instrument for applying a tie, as claimed in claim 20, wherein:
said assembly is entirely of plastic material and the attachments and connections includes detents for snapping together and thereby the instrument is made to be disposable after only one use in the medical application thereof.

22. The instrument for applying a tie, as claimed in claim 13, wherein:
said attachments and said connections of said assembly are interlocking latches for hooking together.

23. A method of making an instrument for applying a tie to items to pull and secure the items together, comprising the steps of:
providing parts which include a first handle and a second handle and a tie guide and a tie gripper for assembly along an axis,
making said second handle to include two flexible legs extending in the direction of said axis and on opposite sides of and spaced apart from said axis,
placing a projection on each said leg and having said projections extend away from said axis,
sliding said tie gripper over said legs and said projections by flexing said legs toward each other and connect said gripper onto said projections, arranging said second handle with a passageway along its entire axial extent and arranging said first handle to be snugly positioned in said passageway and to extend therebeyond and have said handles related to be rotatable together about said axis and relatively axially movable and to have said legs pressed apart for securing said projections connected with said gripper, and connecting said tie guide onto the extending end of said first handle.

24. The method of making an instrument for applying a tie, as claimed in claim 23, including:

releasably connecting said tie gripper to said tie guide for fixed spacing therebetween along said axis and for subsequent relative movement along said axis upon axial movement of said handles.

25. The method of making an instrument for applying a tie, as claimed in claim 23, including:

rockably connecting said tie gripper onto said projections for self-adjusting rocking action of said gripper on said projections in response to tension in said tie.

* * * * *